US008313732B2

(12) United States Patent
Davies et al.

(10) Patent No.: US 8,313,732 B2
(45) Date of Patent: Nov. 20, 2012

(54) FORMOTEROL SUPERFINE FORMULATION

(75) Inventors: Rebecca Jaine Davies, Parma (IT); David Ganderton, Parma (IT); David Andrew Lewis, Parma (IT); Brian John Meakin, Parma (IT); Tanya Kathleen Church, Parma (IT); Gaetano Brambilla, Parma (IT); Alessandra Ferraris, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 164 days.

(21) Appl. No.: 12/873,690

(22) Filed: Sep. 1, 2010

(65) Prior Publication Data

US 2011/0061651 A1 Mar. 17, 2011

Related U.S. Application Data

(63) Continuation of application No. 10/504,151, filed as application No. PCT/EP03/01964 on Feb. 26, 2003, now abandoned.

(30) Foreign Application Priority Data

Mar. 1, 2002 (EP) .................................... 02004786
Oct. 23, 2002 (EP) .................................... 02023589

(51) Int. Cl.
*A61K 9/00* (2006.01)
*A61K 9/08* (2006.01)
*A61K 9/12* (2006.01)
(52) U.S. Cl. ........................................................ 424/45
(58) Field of Classification Search .................... 424/45, 424/46, 489
See application file for complete search history.

(56) References Cited

U.S. PATENT DOCUMENTS

| | | | |
|---|---|---|---|
| 6,004,537 A | 12/1999 | Cavanaugh et al. | |
| 6,150,418 A | 12/2000 | Hochrainer et al. | |
| 6,589,508 B1 * | 7/2003 | Aberg et al. | 424/45 |
| 6,713,047 B1 | 3/2004 | Lewis et al. | |
| 6,716,414 B2 | 4/2004 | Lewis et al. | |
| 6,964,759 B2 | 11/2005 | Lewis et al. | |
| 7,018,618 B2 | 3/2006 | Lewis et al. | |
| 2001/0031244 A1 | 10/2001 | Lewis et al. | |
| 2003/0066525 A1 | 4/2003 | Lewis et al. | |
| 2003/0077230 A1 * | 4/2003 | Blondino et al. | 424/45 |
| 2003/0089369 A1 | 5/2003 | Lewis et al. | |

(Continued)

FOREIGN PATENT DOCUMENTS

| | | |
|---|---|---|
| EP | 1 157 689 | 11/2001 |
| EP | 1787639 A2 * | 5/2007 |
| WO | WO 01/98175 * | 12/2001 |

OTHER PUBLICATIONS

Marino et al. "Scientific evidence and expert clinical opinion for the selection and use of bronchodilators: clinical decision making in the individual patient," in Effective Management of Chronic Obstructive Pulmonary Disease, Chapter 5, Wedzicha J. Ind PW, et al. eds., Aexculapius Medical Press: 2001, pp. 3-23 [ISBN 1-903044197].*

(Continued)

*Primary Examiner* — James H. Alstrum-Acevedo
(74) *Attorney, Agent, or Firm* — Oblon, Spivak, McClelland, Maier & Neustadt, L.L.P.

(57) ABSTRACT

A metal container and a method of preparing a metal container for a pharmaceutical formulation where the active ingredient is formoterol, a stereoisomer of formoterol, and a physiologically acceptable salt of formoterol, in a solution of a liquefied HFA propellant.

32 Claims, 2 Drawing Sheets

Correlation between the assay of formoterol and the residual water content in the formulation $R^2$ is the correlation coefficient deriving from the regression analysis

U.S. PATENT DOCUMENTS

| | | |
|---|---|---|
| 2003/0190287 A1 | 10/2003 | Lewis et al. |
| 2003/0190289 A1 | 10/2003 | Lewis et al. |
| 2003/0206870 A1 | 11/2003 | Lewis et al. |
| 2004/0062720 A1 | 4/2004 | Lewis et al. |
| 2004/0096399 A1 | 5/2004 | Lewis et al. |
| 2004/0184993 A1 | 9/2004 | Lewis et al. |
| 2005/0129621 A1 | 6/2005 | Davies et al. |
| 2005/0154013 A1 | 7/2005 | Davies et al. |
| 2005/0220718 A1 | 10/2005 | Lewis et al. |

OTHER PUBLICATIONS

Vippagunta et al. "Crystalline Solids," Advanced Drug Delivery Reviews, 2001, 48, pp. 3-26.

Armarego, W.L.F. et al. Purification of Laboratory Chemicals, $4^{th}$ Ed., Elsevier: 1996, pp. 28-29.

* cited by examiner $R^2$ is the correlation coefficient deriving from the regression analysis

FORMOTEROL SUPERFINE FORMULATION

CROSS-REFERENCE TO RELATED APPLICATIONS

The present application is a continuation of U.S. Ser. No. 10/504,151, filed on Mar. 10, 2005 now abandoned, which is a National Stage (371) of PCT/EP03/01964, filed on Feb. 26, 2003, which claims priority to EP 02004786.6, filed on Mar. 1, 2002, and EP 02023589.1, filed on Oct. 23, 2002.

FIELD OF THE INVENTION

The present invention relates to a pharmaceutical formulation for use in the administration of a long-acting $\beta_2$-agonist by inhalation.

BACKGROUND OF THE INVENTION

Asthma is a disease which is becoming more prevalent and is the most common disease of childhood. It can be identified by recurrent wheeze and intermittent air flow limitation. Despite many advances in its understanding, said pathology remains a poorly understood and often poorly treated disease. Previously, contraction of airway smooth muscles has been regarded as the most important feature of asthma. Recently there has been a marked change in the way asthma is managed, stemming from the fact that asthma is recognized as a chronic inflammatory disease. Uncontrolled airway inflammation may lead to mucosal damage and structural changes giving irreversible narrowing of the airways and fibrosis of the lung tissue. Therapy should therefore be aimed at controlling symptoms so that normal life is possible and at the same time provide basis for treating the underlying inflammation.

Another respiratory disease whose incidence is steadily increasing throughout the world is chronic obstructive pulmonary disease (COPD). Most patients with COPD have acquired their lung disease through smoking cigarettes. Depending upon trends in tobacco smoking, it is set to rise to fifth most prevalent cause of disability, worldwide by 2020 (Leckie M et al *Exp Opin Invest Drugs* 2000, 9, 3-23).

Chronic obstructive pulmonary disease (COPD) is defined as a disease state characterized by the presence of airflow obstruction due to chronic bronchitis or emphysema.

Chronic bronchitis is characterized by excessive secretion of bronchial mucus, whereas emphysema denotes abnormal, permanent enlargement of air spaces distal to the terminal bronchiole, with destruction of their walls and without obvious fibrosis (American Toracic Society). Each condition is treated as specific diseases.

Chronic obstructive bronchiolitis is due to obstruction of the peripheral airways as a result of inflammation in the bronchioles.

$\beta_2$-Adrenoceptor agonists have been the mainstay of treatment for asthma for many years in view of their prompt bronchodilation effects. Previous researches have also shown that $\beta_2$-agonists have potent anti-inflammatory capabilities, e.g. represented by suppression of release of the pro-inflammatory cytokines.

The first generation drugs such as salbutamol or fenoterol were characterized by a relatively short duration of action which has been considered as a disadvantage particularly for patients with nocturnal asthma. Moreover, they have limited effects in COPD, since this disease involves 'irreversible' airways obstruction. The development of longer acting $\beta_2$-agonists such as formoterol, salmeterol and TA 2005 has therefore been heralded as a major new development in the treatment of asthma. According to some authors, long-acting $\beta_2$-agonists (LABAs) may have acute anti-inflammatory activity in vivo (Johnson M *Clin Exp Allergy* 1992, 22, 177-181; Stelmach I et al *Ann Allergy Asthma Immunol* 2002, 89, 67-73). These drugs are a new interesting therapeutic option for patients with chronic obstructive pulmonary disease (COPD) as well since they have been shown to significantly improve lung function and symptom control.

$\beta_2$-Adrenergic agonists can also stimulate alveolar fluid clearance in several animal species and in ex vivo rat and human lungs. In view of these findings beta-adrenergic agonist therapy has been proposed as a possible treatment for accelerating the resolution of pulmonary oedema in patients with acute pulmonary oedema (Sacuma T et al *Am J Respir Crit Care Med* 1997, 155, 506-512). Treatment with $\beta_2$-agonists may also increase the secretion of surfactant and perhaps exert an anti-inflammatory effect, thus helping to restore vascular permeability of the lung (Ware L et al *New Eng. J Med* 2000, 342, 1334-1349.

Drugs intended for the treatment of lung diseases such as asthma and COPD are currently administered by pulmonary delivery which relies on inhalation of an aerosol through the mouth and throat so that the drug substance can reach the lung. They can be administered as aqueous or hydroalcoholic formulations through a nebuliser, as dry powders by means of Dry Powder Inhalers or in halogenated hydrocarbon propellants. The propellant-based systems require suitable pressurized metered-dose inhalers (pMDIs) which release a metered dose of medicine upon each actuation. The relevant formulations can be in the form of solutions or suspensions. Solution formulations, with respect to suspensions, do not present problems of physical stability of the suspended particles and so could guarantee a higher dose uniformity and reproducibility. As far as the type of propellant is concerned, hydrofluoroalkanes [(HFAs) known also as hydro-fluoro-carbons (HFCs)] would be mandatory propellants as chlorofluorocarbons (known also as Freons or CFCs), which were for many years the preferred propellants aerosols for pharmaceutical use, have been implicated in the destruction of the ozone layer so their use is being phased out. In particular, 1,1,1,2-tetrafluoroethane (HFA 134a) and 1,1,1,2,3,3,3-heptafluoropropane (HFA 227) have been acknowledged to be the best candidates for non-CFC propellants and a number of pharmaceutical aerosol formulations using such HFA propellant systems have been disclosed.

In developing a therapeutic aerosol, the aerodynamic size distribution of the inhaled particles is the most important variable in defining the site of droplet or particle deposition in the lungs of the patient; in short, it will determine whether drug targeting succeeds or fails. See P. Byron, "Aerosol Formulation, Generation, and Delivery Using Nonmetered Systems," Respiratory Drug Delivery, 144-151,144 (CRC Press, 1989).

Thus, a prerequisite in developing a therapeutic aerosol is a preferential particle size.

When the formulation is in the form of suspension, the particle size of the cloud is dominated by the particle size of the suspended drug, defined by the milling/micronization process. When the formulation is in the form of solution, the volumetric contribution of suspended drug particles is absent and much finer liquid droplets clouds, largely defined by the drug concentration in the solution, are generated.

Solid particles and/or droplets in an aerosol formulation can be characterized by their mass median aerodynamic diameter (MMAD, the diameter around which the mass aerodynamic diameters are distributed equally).

Particle deposition in the lung depends largely upon three physical mechanisms:
  i) impaction, a function of particle inertia;
  ii) sedimentation due to gravity; and
  iii) diffusion resulting from Brownian motion of fine, sub-micrometer (<1 microns) particles. The mass of the particles determines which of the three main mechanisms predominates.

For aerosol therapy of drugs which topically act on the smooth muscle of the conducting airways, and in particular for $\beta_2$-agonists, it has been reported in the past that particles should preferentially deposit in the upper- to mid-pulmonary region (bronchiole region), so they should have a MMAD of about 1.5(2.0) to about 5.0 microns, preferably approximately 3 microns (Zanen P et al *Int J Pharm* 1994, 107, 211-217; *Int J Pharm* 1995, 114, 111-115; *Thorax*, 1996, 51, 977-980).

In fact, particles having aerodynamic diameters of greater than about 5 microns generally do not reach the lung since they tend to impact the back of the throat and are swallowed and possibly orally absorbed, while particles smaller than 1.5 (2.0) micron, i.e., about 0.5 to about 2 microns, capable of reaching the alveolar region, have been considered undesirable because they can be absorbed into the bloodstream and might enhance the undesired systemic effects of the drugs. Particles having diameters smaller than about 0.5 microns have been generally considered as not therapeutically useful as they can be exhaled.

Accordingly, pMDI formulations of $\beta_2$-agonist have traditionally been formulations able to deliver particles whose larger fraction is comprised between 2 and 5 microns and the amount of those below 1 micron is very limited since the former are small enough to reach the upper- to mid-pulmonary region, but are too large to reach the alveoli. This is also the inherent particle size of the formulation in the form of suspensions as conventional micronization (air-jet milling) of pure drug substance can reduce the drug particle size to about 2-3 microns.

On the other hand, it is known that the density of the beta-adrenergic receptors is higher in the distal tract of the bronchioles (Barnes P et al *Am Rev Respir Dis* 1983, 127, 758-762), a region which is better reached by smaller particles. Moreover inflammation in asthma in not merely confined to the large central airways but also extends to small peripheral airways. The eosinophilic inflammation process which has been seen to be associated to asthma concerns both the bronchial and the alveolar districts (Wang S J *Immunol* 2001, 166, 2741-2749). Recently, Martin R in *J Allergy Clin Immunol* 2002, 109 (Suppl 2), 447-460 reported that distal lung diseases appear to increase the risk of recurrent asthma exacerbation, while disease-related anatomic changes in the small airways of the distal lung are prominent in fatal asthma. In this respect, in his opinion, the administration of drug with particles of a diameter of about 1 micron (referred as "extrafine" aerosols) could be advantageous. The clinical significance of distal lung disease makes this region an important therapeutic target so particles able to reach and deposit into such region could better contribute to the management of the disease. It has been also reported that, among the particles smaller than 0.5 micron, those with a diameter less or equal than 0.3 micron, preferably between 5 and 300 nm, can be deposited in the alveolar region of the lung by sedimentation. This range of particle has been referred to in the literature as "ultrafine" particles.

"Ultrafine" particles generated from di-2-ethylhexyl sebacate (DEHS) as a model, have also been reported to have a good airway penetration (Anderson P et al *Chest* 1990, 97, 1115-1120). Therefore medicinal aerosol particles having a diameter <0.1 µm can be particularly effective in case of airway obstruction in asthmatic subjects wherein the pathology is associated with mucus hypersecretion which hinders the diffusion of the drug or in patients affected by obstructive lung diseases such as COPD. Intuitively indeed, one would expect the reduction in the lumen of airways by mucus and permanent constriction would require finer clouds for perfusion.

In virtue of the inherent anti-inflammatory properties of LABAs, relevant formulations capable of delivering a significant fraction of fine particles would be expected to be of great advantage in patients affected by broncho-pulmonary obstructive diseases. Amirav I et al in *J Nucl Med* 2002, 43, 487-491 emphasize the need for improvement in aerosol delivery by targeting narrow peripheral airways with superfine aerosols in the treatment of inflammation airways diseases and in particular in acute bronchiolitis.

Formoterol, {(R,R)-(±)-N-[2-hydroxy-5-[1-hydroxy-2-[[2-(4-methoxy-phenyl)-1-methylethyl]amino]ethyl]-phenyl]formamide} is a selective $\beta_2$-receptor agonist, exerting, upon inhalation, a prolonged bronchodilation up to 12 hours. It is currently marketed as CFC formulation (Foradil®).

In view of the above considerations, it would be highly advantageous to provide highly efficient formoterol formulation to be administered by pMDI characterized by a deeper lung penetration wherein, unexpectedly, the systemic exposure is not significantly higher than that of the formulations currently on the market.

DESCRIPTION OF THE INVENTION

Figure 1:
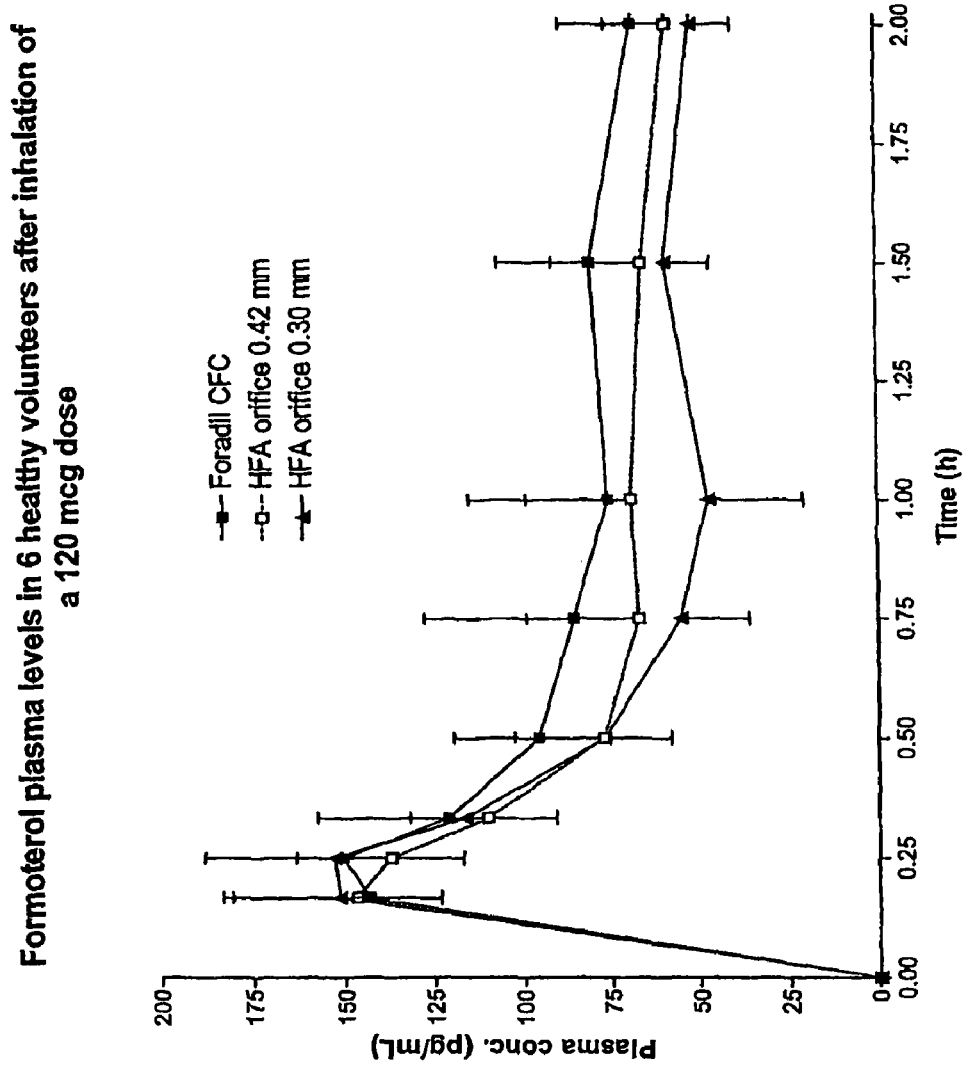
FIG. 1 shows the plasma concentration of formoterol in the first two hours as described in Example 2.

The object of the present invention is to provide a pharmaceutical aerosol solution formulation to be administered by pMDI, having a suitable shelf-life for pharmaceutical use, comprising formoterol as active ingredient, a HFA propellant and a suitable amount of co-solvent wherein the active ingredient is completely dissolved in the propellant-cosolvent system and the amount of residual water is less than 1500 ppm on the total weight of the formulation. Said solution is able of providing on actuation of the formulation a fraction of particles equal or less than 1.1 micron of at least 30% as defined by the content stages S6-AF of an Andersen Cascade Impactor relative to the total amount of the fine particle dose collected in the stages S3-AF of the impactor.

The formulation of the invention is able to deliver a significant fraction of particles having a diameter equal or less than 1.1 micron, comprising both extrafine particles, according to the definition of Martin R in *J Allergy Clin Immunol* 2002, 109 (Suppl 2), 447-460 and particles having a diameter equal or less than 0.3 micron (ultrafine particles, according to the definition of other authors). By virtue of these characteristics the formulation of the invention will be hereinafter referred to as superfine formulation.

In the prior art sub-micron aerosol formulations (including HFA formulations) have only been reported as microemulsions containing surface active agents such as lecithin (WO 01/78689, WO 00/27363; Dickinson P et al *J Drug Target* 2001, 9, 295-302).

As a preferred aspect of the present invention, we provide a pharmaceutical aerosol formulation comprising 0.003-0.192% w/v formoterol or one of its pharmaceutically acceptable salt such as fumarate as active ingredient in solution in a liquefied HFA propellant and a co-solvent preferably selected from a pharmaceutically acceptable alcohol, characterized in that the fraction of particles equal or less than 1.1 micron is higher or of at least 30% and the content of humidity as determined by Karl-Fischer method is less than 1500 ppm.

Advantageously the pH of the formulation is to between 2.5 and 5.0 as determined in the model vehicle system reported in EP 1157689.

It has been surprisingly found that following the administration of formoterol solution formulations with a significant fraction of particles of or below 1.1 micron the plasma levels of the active ingredient in the earlier phase of absorption compare to those of the CFC reference formulation on the market (Foradil) which has a small fraction of particles below 1.1 micron.

Moreover, it has been found that the total systemic exposure corresponding to the fraction of drug absorbed through the lung plus the amount swallowed and absorbed through the gut is slightly inferior to that of the reference formulation, making the formulation of the invention potentially better tolerated.

A low systemic exposure of formoterol is particularly advantageous, since the extent of drug absorbed into the blood stream is responsible of the side effects on the cardiovascular system.

As reported by the applicant in EP1157689, through the adjustment of the apparent pH it is possible to dramatically improve the chemical stability of formoterol in solution in a HFA propellant and a cosolvent. The addition of a low amount of isopropyl myristate may further improve the chemical stability of the compound.

It has now been found, as demonstrated in Example 3, that formoterol in this kind of formulation is extremely sensitive to the residual humidity and for amount of water higher than 1500 ppm on the total weight of the formulation its content decreases to such a level (less than 90% w/w) which is not longer acceptable for pharmaceutical purposes. The influence of a residual water content on the chemical stability of the active ingredient is particularly dramatic in high efficiency superfine formulations lacking of isopropyl myristate.

In the prior art HFA solution formulations of $\beta_2$-agonists for aerosol delivery through pressurized metered-dose inhalers have been disclosed.

WO 94/13262 in the name of Boehringer Ingelheim provides aerosol solution formulations comprising a medicament, an HFC propellant, a cosolvent and an inorganic or an organic acid as a stabiliser for preventing the chemical degradation of the active ingredient. Most examples relate to ipratropium bromide, an anticholinergic drug. Although formoterol is cited among other active ingredients, no example is reported. As far as $\beta_2$-agonists are concerned, only formulations containing fenoterol, a short acting derivative not chemically related to formoterol are exemplified. Furthermore, apart from ipratropium bromide, in WO 94/13262 no guidance is given with respect to the amount of acid which has to be added in order to stabilise the medicaments without compromising the stability of the whole composition in the can. The only hint can be found on page 5, lines 15 to 16 which says that an amount of inorganic acid should be added to obtain a pH value from 1 to 7, so a very broad and generic range. As far as the water content is concerned, in the application it is stated that a small amount of water (up to about 5% by weight) may also be present in the propellant/cosolvent system. In the case of ipratropium bromide, it is reported that addition of 1% water reduces the decomposition due to dehydration. The document is silent about the effects of water on $\beta_2$-agonists and especially about the effect that an amount of residual water higher than 1500 ppm might have on the chemical stability of formoterol in solution in the propellant/cosolvent system.

WO 98/34596 in the name of 3 M refers to solution formulations containing a propellant and a physiologically acceptable polymer which could help the solubilisation and the stability as well of the active ingredients.

WO 98/34595 in the name of Jago Research refers to aerosol formulations in the form of solutions or suspensions in which the propellant is a mixture of a HFA and carbon dioxide. The presence of carbon dioxide can improve either physical and chemical stability of active compounds. Formoterol is cited among the active compounds which can be used but no examples are reported.

WO 00/06121 in the name of Jago Research refers to propellant mixtures for aerosol containing dinitrogen monoxide and a hydrofluoroalkane in the preparation of suspension and solution aerosols. The use of dinitrogen monoxide may improve the stability at storage of oxidation-sensitive active ingredients. As far as LABAs such as formoterol fumarate and salmeterol xinafoate, only examples referred to suspensions are reported.

WO 99/65460 in the name of Baker Norton claims pressurised MDI's containing stable formulations of a $\beta_2$-agonist drug in suspension or solution. Examples refer to solutions of formoterol fumarate containing an HFA propellant and ethanol as a co-solvent, filled in conventional aluminium or plastic coated glass cans. Samples stored under accelerated conditions (40° C., 75% relative humidity) for a very short period, one month, exhibited about 10% loss of drug. According to the pharmaceutical guideline ICH Q1A "Stability Testing of new Active Substances (and Medicinal Products)" of October 1993, a 5% change in assay of the active ingredient from its initial value does not meet the criteria of acceptance. Moreover, even said document is silent about the dramatic effect of residual water on the chemical stability of formoterol and its salts.

In WO 98/56349 the applicant described solution compositions for use in an aerosol inhaler, comprising an active material, a propellant containing a hydrofluoroalkane (HFA), a co-solvent and further comprising a low volatility component to increase the mass median aerodynamic diameter (MMAD) of the aerosol particles on actuation of the inhaler. In some cases a small quantity of water may be added to the composition to improve the solution of the active material and/or the low volatility component in the cosolvent.

In EP 1157689 the applicant disclosed aerosol pharmaceutical compositions comprising a $\beta_2$-agonist belonging to the class of phenylalkylamino derivatives in solution in a HFA propellant, a co-solvent whose apparent pH has been adjusted to between 2.5 and 5.0 in order to guarantee an adequate shelf-life. In a particular embodiment of the invention, isopropyl myristate (IPM) as a low-volatility is added in order to either increase the MMAD of the aerosol particles and further improving the stability of the formulation. As far as the role of water is concerned, it is only generically stated that humidity, in the case of certain active ingredients such as formoterol, could be detrimental to the (chemical) stability during storage. Formoterol-based HFA 134a solution formulations containing 12% w/w ethanol with or without 1.0% w/w IPM are reported in example 5. No guidance is given in EP 1157689 for further improving the stability of the relevant formulations by strictly controlling the residual amount of water, in particular when IPM, which improves the chemical stability of formoterol, is avoided. There is no preference in EP 1 157 689 for compositions containing IPM or not.

As mentioned above, the formulations of the invention can also comprise a further active ingredient. In particular, the addition of a corticosteroid to a long-acting $\beta_2$-agonist gives optimal control of asthma in most patients and relevant fixed combinations are increasingly used as a convenient controller in patients with persistent asthma. It has also been reported that each class of drug enhances the beneficial actions of the other. In fact, corticosteroids increase the expression of $\beta_2$-receptors and protect them against down-regulation in response to long-acting $\beta_2$-agonist exposure, whereas $\beta_2$-agonist may enhance the anti-inflammatory actions of corticosteroids (Barnes P et al. Eur Respir J 2002, 19, 182-191).

Accordingly, another object of the present invention is to provide highly efficient formoterol formulations further comprising a steroid. The high fraction of superfine particles of the formulation of the invention can allow both drugs to reach the small peripheral airways region in such a way as to better exercise their synergic effects in distal lung diseases (vide supra). Moreover, in view of the aforementioned characteristics, it might be possible to develop formulations comprising fixed combinations of formoterol and a steroid wherein the latter one could be present in a lower dose, by maintaining the same therapeutic effect.

A further aspect of the present invention is to provide highly efficient formoterol formulations in combination with an anticholinergic atropine-like derivative such as ipratropium bromide, oxitropium bromide and tiotropium bromide in order to provide a medicament particularly effective for the treatment of COPD.

It is also provided a method of filling an aerosol inhaler with a composition of the invention, the method comprising:
 (a) preparation of a solution of one or more active ingredients in one or more co-solvents
 (b) optionally adjusting the pH of the solution
 (c) filling of the device with said solution
 (d) crimping with valves and gassing
 (e) adding a propellant containing a hydrofluoroalkane (HFA)

A still further aspect of the invention comprises the use of the formoterol fully dissolved in the propellant/co-solvent system and capable of providing on actuation a fraction of at least 30% of emitted particles with an aerodynamic diameter equal or less than 1.1 microns, for the treatment of respiratory disorders such as asthma and COPD.

In view of its technical feature of providing on actuation a fraction of particles with an aerodynamic diameter of less than 1.1 micron, of at least 30%, the formulation of the invention can be particularly effective for the treatment of asthma, COPD and, generally, of airway obstruction conditions wherein the pathology is associated with mucus hypersecretion which hinders the diffusion of the drug.

Furthermore, it may be clinically useful as a treatment to hasten the resolution of alveolar oedema and of surfactant-deficiency related diseases such as acute lung injury (ALI) and acute respiratory distress syndrome (ARDS).

DETAILED DESCRIPTION OF THE INVENTION

The aerosol formulations of the invention comprise an HFA propellant and a co-solvent wherein the active ingredient is fully dissolved in such a way that the formulations are able of providing on actuation a fraction of emitted particles of equal or less than 1.1 microns higher or equal to 30% as defined by the content stages S6-AF of an Andersen Cascade Impactor relative to the total fine particle dose collected in the stages S3-AF of the impactor, advantageously higher than 40%, preferably higher than 50%, more preferably higher than 60%, even more preferably higher than 70%. Advantageously, the formulations of the invention are free of other excipients such as surfactants besides the solubilisation agent and the propellant.

Examples of HFA propellants include 1,1,1,2-tetrafluoroethane (HFA134a) and 1,1,1,2,3,3,3-heptafluoro-n-propane (HFA227) and mixtures thereof. The preferred propellant is 1,1,1,2-tetrafluoroethane (HFA134a). An alternative propellant of interest is 1,1,1,2,3,3,3-heptafluoro-n-prop-ane (HFA227).

The co-solvent is selected from the group of lower alkyl ($C_1$-$C_4$) alcohols, polyols, polyalkylene glycols and their combinations. Other suitable co-solvents are (poly)alkoxy derivatives including polyalkoxy alcohols, [such as 2-(2-ethoxyethoxy) ethanol available under the trademark Transcutol®].

Preferably the co-solvent is an alcohol. The preferred one is ethanol. Since the presence of water has to be avoided as much as possible, the co-solvent will be even more preferably anhydrous ethanol, optionally dried on 3 Å sieves. The concentration of the co-solvent (e.g. ethanol) will vary depending on the final concentration of the active ingredients in the formulation and on the propellant. The amount of ethanol should not exceed around 40% w/w of the total weight of the formulation. Advantageously it is comprised between 5 and 30% w/w, preferably between 10 and 20% w/w, even more preferably between 12 and 15% w/w.

Active ingredients which may be used in the aerosol compositions of the invention are formoterol and stereoisomers, physiologically acceptable salts and solvates thereof.

Suitable physiological salts include chloride, bromide, sulphate, phosphate, maleate, fumarate, tartrate, citrate, benzoate, mesilate, ascorbate, salicylate, acetate, succinate, lactate, glutarate or gluconate.

In one of the embodiments of the invention, we prefer to use (R,R)-(±) formoterol more preferably in the form of fumarate salt.

Said active ingredient can be used alone or in combination with steroids such as beclometasone dipropionate (BDP), flunisolide, mometasone furoate, fluticasone propionate, ciclesonide, budesonide and its 22R-epimer, with anticholinergic atropine-like derivatives such as ipratropium bromide, oxitropium bromide, tiotropium bromide or with drugs useful for the management of respiratory diseases such as methylxanthines, anti-leukotrienes and phosphodiesterase inhibitors.

The preferred combinations concern formoterol and BDP, budesonide or its 22R-epimer.

The concentration of formoterol in the HFA formulation, will depend on the therapeutic amount to be delivered preferably in one or two actuations.

In the foregoing drug concentrations are given as (w/v) and as fumarate salt. The corresponding percentages as (w/w) can be calculated by determining the density of the vehicle.

The formulation according to the invention will be filled in a canister fitted with a suitable metering valve. We prefer that the formulation is actuated by a metering valve capable of delivering a volume of between 25 μl and 100 μl, e.g. 50 μl or 63 μl. 100 μl is also suitable.

The concentration of formoterol will vary between 0.003 and 0.192% w/v, preferably between 0.006 and 0.048% w/v in order to deliver 3 to 48 µg, preferably 6 or 12 µg per actuation.

For instance, for a 12 µg dose, when a 100 µl metering volume is used, the final concentration of formoterol fumarate delivered per actuation would be 0.012% w/v; where a 50 µl metering volume is used, the final concentration of formoterol fumarate would be doubled, e.g. 0.024% w/v and where a 63 µl metering volume is used, which is the preferred one, the final concentration would be 0.019% w/v.

The intended dose regimen is twice or once daily, where the suitable daily dose is in the range of 6 to 48 µg.

The apparent pH range is advantageously between 2.5 and 5.0, preferably between 3.0 and 4.5. Strong mineral acids preferably selected from hydrochloric, nitric, phosphoric acid can be used to adjust the apparent pH, more preferably hydrochloric acid.

The amount of acid to be added to reach the desired apparent pH will be pre-determined in the model vehicle reported in EP 1157689 and it will depend on the type and concentration of the active ingredient and the amount of the co-solvent. For 0.019% w/v formoterol fumarate solutions in 12% w/w ethanol and HFA 134a q.s. to about 10 ml, an amount comprised between 3.85 and 4.85 µl of 1 M HCl is advantageously added, preferably between 4.15 and 4.55 µl of 1 M HCl, with the optimum of 4.35 µl. In more general terms, the concentration of 1 M HCl is between 0.030% w/w and 0.045% w/w, preferably between 0.035% and 0.040% w/w on the total weight of the formulation.

The amount of water is lower than 1500 ppm, preferably lower than 1000 ppm, even more preferably lower than 500 ppm on the total weight of the formulation.

The formulations of the invention will be filled into canisters suitable for delivering pharmaceutical aerosol formulations such as plastic or plastic coated glass bottle or preferably a metal can, for example an aluminium can. The formulations can also be filled in canisters having part of all of the internal surfaces made of anodised aluminium, stainless steel or lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene, polyether sulfone and a copolymer fluorinated-ethylene-propylene polyether sulfone. Other suitable coatings could be polyamide, polyimide, polyamideimide, polyphenylene sulfide or their combinations.

To further improve the stability, cans having a rim with rounded edges, preferably a rolled neck or rolled-in rim, a part or full rollover rim can be used according to the teaching of the co-pending application n. WO 02/72448.

The canister is closed with a metering valve. The metering valves are designed to deliver a metered amount of the formulation per actuation and incorporate a gasket to prevent leakage of propellant through the valve.

The gasket may comprise any suitable elastomeric material such as for example low density polyethylene, chlorobutyl, black and white butadiene-acrylonitrile rubbers, butyl rubber, neoprene, EPDM (a polymer of ethylenepropylenediene monomer) and TPE (thermoplastic elastomer). EPDM and TPE rubbers are preferred. EPDM rubbers are particularly preferred. Suitable valves are commercially available from manufacturers well known in the aerosol industry, for example, from Valois, France (eg. DF10, DF30, DF60), Bespak plc, UK (eg. BK300, BK356, BK357) and 3M-Neotechnic Ltd, UK (eg. Spraymiser). The DF31 valve of Valois, France is also suitable. Valve seals, especially the gasket seal, and also the seals around the metering chamber, will preferably be manufactured of a material which is inert to and resists extraction into the contents of the formulation, especially when the contents include ethanol.

Valve materials, especially the material of manufacture of the metering chamber, will preferably be manufactured of a material which is inert to and resists distortion by contents of the formulation, especially when the contents include ethanol. Particularly suitable materials for use in manufacture of the metering chamber include polyesters e.g. polybutyleneterephthalate (PBT) and acetals, especially PBT.

Materials of manufacture of the metering chamber and/or the valve stem may be fluorinated, partially fluorinated or impregnated with fluorine containing substances in order to resist drug deposition.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method a metering valve is crimped onto an aluminum can to form an empty canister. The medicament is added to a charge vessel and a mixture of ethanol, optionally water and liquefied propellant is pressure filled through the charge vessel into a manufacturing vessel. An aliquot of the formulation is then filled through the metering valve into the canister.

In an alternative process, an aliquot of the liquefied formulation is added to an open canister under conditions which are sufficiently cold that the formulation does not vaporize, and then a metering valve crimped onto the canister.

In an alternative process, an aliquot of medicament dissolved in the solubilising agent is dispensed into an empty canister, a metering valve is crimped on, and then the propellant is filled into the canister through the valve. Preferably, the processes are carried out an in inert atmosphere, for instance by insufflating nitrogen, in order to avoid the uptake of humidity from the air.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator.

In a typical arrangement the valve stem is seated in a nozzle block which has an orifice leading to an expansion chamber. The expansion chamber has an exit orifice which extends into the mouthpiece. Actuator (exit) orifice diameters in the range 0.15-0.45 mm especially 0.2-0.45 mm are generally suitable e.g. 0.25, 0.30, 0.33 or 0.42 mm. 0.22 mm is also suitable. For certain formulations it would be useful to utilize laser-drilled actuator orifices having a diameter ranging from 0.10 to 0.22 mm, in particular from 0.12 to 0.18 mm as those described in the co-pending application n. EP 1130521.6.

The use of such fine orifices also increases the duration of cloud generation and lowers its velocity. These changes facilitate the coordination of cloud generation with the slow inspiration of the patient.

Since the ingress of water into the formulation needs to be avoided, it may be desired to overwrap the MDI product in a package, preferably flexible, capable of resisting water ingress. It may also be desired to incorporate a material within the packaging which is able to adsorb any propellant and co-solvent which may leak from the canister. (e.g. a molecular sieve).

The aerodynamic particle size distribution of each tested formulation of the invention can be characterized using a Multistage Cascade Impactor according to the procedure described in European Pharmacopoeia $2^{nd}$ edition, 1995, part V.5.9.1, pages 15-17. In this specific case, an Andersen Cascade Impactor (ACI) was utilized operating at a flow rate of 28.3 l/min. Deposition of the drug on each ACI plate was determined by high pressure liquid chromatography (HPLC). Mean delivered dose was calculated from the cumulative deposition in the ACI. Mean respirable dose (fine particle dose) was obtained from the deposition on Stages 3 (S3) to filter (AF) corresponding to particles ≦4.7 microns, divided by the number of actuation per experiment, while mean "superfine" dose was obtained from the deposition on Stages 6 to filter corresponding to particles ≦1.1 microns.

The delivery characteristics of the formulation are reported in Table 1 in comparison with the reference CFC formulation currently available on the market (Foradil). In particular the following parameters are reported: i) nominal dose: theoretical dose per single actuation; ii) delivered dose: amount of active particles deposited into the all ACI stages; iii) respirable dose (fine particle dose): amount of active particles of size equal or less than 4.7 microns (S3-AF); iv) respirable fraction (fine particle fraction): ratio between the respirable dose and the delivered dose; v) "superfine" dose: amount of active particles equal or less than 1.1 microns (S6-AF); iv) "superfine" fraction: ratio between the "superfine" dose and the respirable dose.

TABLE 1

Delivery characteristics of the formoterol HFA solution formulations of the Ex. 1.

|  | Nominal Dose (µg) | Delivered dose (µg) | Respirable dose (µg) | Respirable fraction (%) | Superfine dose (µg) | Superfine Fraction (%) |
| --- | --- | --- | --- | --- | --- | --- |
| Formulation Ex1 Act 0.30 mm | 12 | 10.02 | 3.31 | 32.5 | 2.53 | 76.4 |
| Formulation Ex 1 Act 0.42 mm | 12 | 10.84 | 2.14 | 19.7 | 1.57 | 73.3 |
| Foradil | 12 | 11.1 | 5.70 | 51.4 | 1.18 | 20.7 |

Administration of the formulations of the invention may be indicated for the treatment of mild, moderate or severe, acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis can also benefit of this kind of formulation.

The invention is illustrated with reference to the following examples.

Example 1

Superfine Formoterol HFA Formulation

A formulation was prepared with the composition as follows:

|  | Amounts | | Nominal dose |
| --- | --- | --- | --- |
|  | Per unit | | |
| Components |  | % | µg |
| Formoterol fumarate | 1.92 mg | 0.019 w/v | 12 |
| Anhydrous ethanol | 1416.7 mg | 12 w/w | — |
| HCl 1M | 4.40 mg* | 0.037 w/w | — |
| HFA 134a (q.s. to 10.09 ml) | 11808 mg | — | — |

*equivalent to 4.35 µl

The formulation (120 actuations/canister, overage of 40 actuations) was filled in standard aluminum canisters (two stage pressure filling) under pressure and fitted with a metering valve having a 63 µl metering chamber. Two actuators were used with orifice diameter of 0.30 and 0.42 mm. Results were obtained as a mean of 2 cans.

The aerodynamic particle size distribution was determined by ACI, according to the description on page 17 lines 4 to 12.

The results show that the reference formulation upon actuation shows a higher respirable fraction, while the formulations of the invention give rise to a dramatically higher percentage of particles with a diameter equal or less than 1.1 microns, particles which are thought to better reach the distal tract of the bronchioles.

Example 2

Pharmacokinetics Study

The aim of the study was to evaluate the pharmacokinetics of formoterol in 6 healthy volunteers after single administration of the formoterol formulations of Example 1 at 120 µg dose (10 shots×12 µg/shot) in comparison with the marketed CFC formulation (Foradil). The experimental protocol is reported as follows:

Treatments

Foradil CFC 120 .mu.g. (10 shots×12 .mu.g/shot): Reference formulation

Formoterol/HFA orifice 0.42 mm 120 .mu.g. (10 shots×12 µg/shot): Test formulation Formoterol/HFA orifice 0.30 mm 120 .mu.g. (10 shots×12 µg/shot): Test formulation The study was a single dose cross-over study; subjects received the drug at 8 a.m. The wash-out among different treatments was of at least 1 weeks. Patients were instructed to take 10 doses. Time 0 for each dose was defined as the time when the MDI is first actuated.

Bioanalysis

Assay of formoterol was carried out employing HPLC/MS validated method with a LOQ of 2 pg/mL.

The pharmacokinetics parameters are reported in Table 2 while in FIG. 1 the plasma concentration in the first two hours are shown.

TABLE 2

Pharmacokinetics parameters

| | Foradil CFC | Formoterol HFA of Ex. 1 0.42 mm | Formoterol HFA of Ex. 1 0.30 mm |
|---|---|---|---|
| $C_{max}$ (pg ml$^{-1}$) | 159 ± 34 | 150 ± 36 | 158 ± 32 |
| $AUC_{(0-20\ min)}$ (pgml$^{-1}$ * h) | 35.4 ± 9.0 | 34.3 ± 7.3 | 36.5 ± 7.3 |
| $AUC_t$ (pgml$^{-1}$ * h) | 655 ± 153 | 611 ± 103 | 578 ± 98 |

$C_{max}$ is the maximum plasma concentration
$AUC_{0-20\ min}$ is the area under the curve of the plasmatic levels from time 0 h to 20 minutes;
$AUC_t$ is the area under the curve of the plasmatic levels from time 0 h to the last measurable data point.

The results demonstrate that the formoterol formulations of Example 1, despite their different particle size distribution characterized by a high fraction of particles equal or less than 1.1 μm, show plasma levels in the 0 to 20 min time interval, that reflects the amount of drug absorbed from the lung, comparable to the reference formulation.

Surprisingly, the total systemic exposure (see FIG. 1), corresponding to the fraction of drug absorbed through the lung plus the amount swallowed and absorbed through the gut, is slightly lower with the formulations of the invention than with the reference one. This may be considered as an advantage since for a drug that exert its activity at the lung level, a reduced systemic exposure may translate in a decreased risk of undesired systemic effects.

In a preliminary clinical trial it was also demonstrated that the formulations of Examples 1 and 2 have a bronchodilator action equivalent to that of the reference formulation in CFC propellant and a good tolerability.

Example 3

Effect of the Residual Humidity on the Formoterol Assay

The formulation of Example 1 filled in standard aluminum cans was stored in different conditions (25° C., 40° C.) and for different times (0, 3, 6 months).

The assay of formoterol was determined by HPLC while the water content was determined by Karl-Fischer method.

Figure 2:
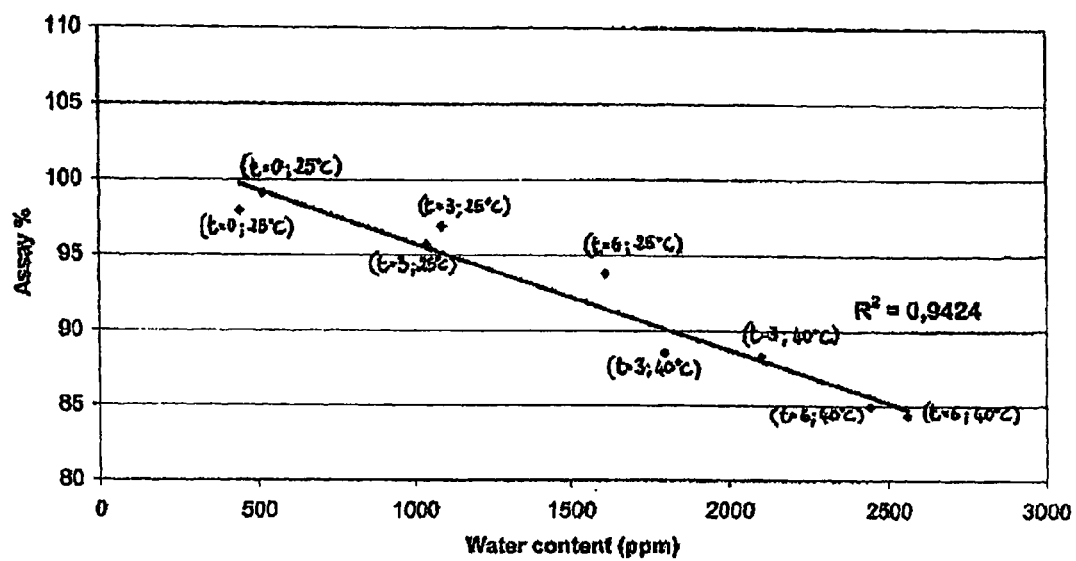
FIG. 2 shows the effect of residual humidity in the assay of formoterol and illustrates an inverse linear correlation between the assay of formoterol and the residual amount of water as described in Example 3.

The results, reported in FIG. 2, show an inverse linear correlation between the assay of formoterol and the residual amount of water. The numbers between brackets refer to time and temperature condition, respectively. The formoterol assay for a residual humidity lower than 1500 ppm meets the requirements of the ICH guideline Q1A, whereas for a residual humidity higher than 1500 ppm, the assay decreases below 90%.

Example 4

Stability Study

A stability study on a formulation prepared according to the Example 1 was initiated storing the cans upright and inverted at 5° C.

Assays of formoterol and its main related substances (degradation products) were determined by HPLC.

At twelve months the formoterol assay is higher than 95% and therefore meets the requirements of the ICH guideline Q1A. Under these storage conditions, the water content maintains below 1000 ppm.

The storage conditions are the same of that of the reference product Foradil® whereas the shelf life is better, as the latter has to be kept at refrigerator temperature for maximum nine months.

What we claim is:

1. A metal container, which contains a pharmaceutical formulation,
   wherein said pharmaceutical formulation comprises:
   an active ingredient selected from the group consisting of formoterol, a stereoisomer of formoterol, and a physiologically acceptable salt of formoterol, in a solution of a liquefied HFA propellant;
   ethanol; and
   hydrochloric acid,
   wherein said ethanol is in anhydrous form and is present in a concentration between 10% and 20% w/w, and said hydrochloric acid is present in an amount equal to between 0.030% and 0.045% w/w of 1M hydrochloric acid, and any water present in said pharmaceutical formulation is present in an amount lower than 1500 ppm, based on the total weight of said pharmaceutical formulation, and said container is a standard aluminum can.

2. A container according to claim 1, wherein any water is present in said pharmaceutical formulation is present in an amount lower than 1000 ppm.

3. A container according to claim 1, wherein any water is present in said pharmaceutical formulation is present in an amount lower than 500 ppm.

4. A container according to claim 1, wherein said active ingredient is present in said pharmaceutical formulation in a concentration between 0.003 and 0.192% w/v.

5. A container according to claim 1, wherein said active ingredient is present in said pharmaceutical formulation in a concentration between 0.006 and 0.048% w/v.

6. A container according to claim 1, wherein said propellant comprises one or more hydrofluoroalkanes selected from the group consisting of HFA 134a and HFA 227.

7. A container according to claim 1, wherein said pharmaceutical formulation comprises 0.012-0.048% w/v formoterol fumarate, 12% w/w anhydrous ethanol, hydrochloric acid in an amount equal to 0.037% w/w of 1 M hydrochloric acid, and HFA 134a.

8. A container according to claim 1, wherein said pharmaceutical formulation further comprises a steroid or an anticholinergic drug.

9. A container according to claim 8, wherein said pharmaceutical formulation comprises at least one steroid selected from the group consisting of beclomethasone dipropionate, fluticasone propionate, budesonide, and the 22R-epimer of budesonide.

10. A container according to claim 8, wherein said pharmaceutical formulation comprises at least one anticholinergic drug selected from the group consisting of ipratropium bromide, oxitropium bromide, and tiotropium bromide.

11. A container according to claim 1, wherein said ethanol is present in said pharmaceutical formulation in an amount between 10 and 15% w/w.

12. A container according to claim 1, wherein said active ingredient is
    (R,R)(−)formoterol fumarate.

13. A container according to claim 1, wherein said hydrochloric acid is present in said pharmaceutical formulation in an amount equal to between 0.035% w/w and 0.040% w/w of 1M hydrochloric acid.

14. A container according to claim 1, wherein said pharmaceutical formulation comprises 0.006-0.048% w/v formoterol fumarate, 10-15% w/w anhydrous ethanol, hydrochloric acid in an amount equal to 0.030-0.045% w/w of 1M hydrochloric acid, and HFA 134a.

15. A pressurized metered dose inhaler, comprising a container, which contains a pharmaceutical formulation,
wherein said pharmaceutical formulation comprises:
an active ingredient selected from the group consisting of formoterol, a stereoisomer of formoterol, and a physiologically acceptable salt of formoterol, in a solution of a liquefied HFA propellant;
ethanol; and
hydrochloric acid,
wherein said ethanol is in anhydrous form and is present in a concentration between 10% and 20% w/w, and said hydrochloric acid is present in an amount equal to between 0.030% and 0.045% w/w of 1M hydrochloric acid, and any water present in said pharmaceutical formulation is present in an amount lower than 1500 ppm based on the total weight of the formulation, and said container is a standard aluminum can, and
wherein said pressurized metered dose in haler delivers on actuation, a fraction of fine particles of active ingredient with a size equal to or less than 1.1 μm which is higher than or equal to 30% as defined by the content of the stages S6-AF of an Andersen Cascade Impactor, relatively to the content of the stages S3-AF.

16. A pressurized metered dose inhaler according to claim 15 wherein the fraction of fine particles of active ingredient with a size equal to or less than 1.1 μm delivered on actuation of the inhaler is higher than 40%.

17. A pressurized metered dose inhaler according to claim 15 wrapped in a package capable of resisting water ingress.

18. A pressurized metered dose inhaler according to claim 17 wherein the package further incorporates a molecular sieve to adsorb any propellant or co-solvent which may leak from the container.

19. A pressurized metered dose inhaler according to claim 15, wherein any water is present in said pharmaceutical formulation is present in an amount lower than 1000 ppm.

20. A pressurized metered dose inhaler according to claim 15, wherein any water is present in said pharmaceutical formulation is present an amount lower than 500 ppm.

21. A pressurized metered dose inhaler according to claim 15, wherein said active ingredient is present in said pharmaceutical formulation in a concentration between 0.003 and 0.192% w/v.

22. A pressurized metered dose inhaler according to claim 15, wherein said active ingredient is present in said pharmaceutical formulation in a concentration between 0.006 and 0.048% w/v.

23. A pressurized metered dose inhaler according to claim 15, wherein said propellant comprises one or more hydrofluoroalkanes selected from the group consisting of HFA 134a and HFA 227.

24. A pressurized metered dose inhaler according to claim 15, wherein said pharmaceutical formulation comprises 0.012-0.048% w/v formoterol fumarate, 12% w/w anhydrous ethanol, hydrochloric acid in an amount equal to 0.037% w/w of 1M hydrochloric acid, and HFA 134a.

25. A pressurized metered dose inhaler according to claim 15, wherein said pharmaceutical formulation further comprises a steroid or an anticholinergic drug.

26. A pressurized metered dose inhaler according to claim 25, wherein said pharmaceutical formulation comprises at least one steroid selected from the group consisting of beclomethasone dipropionate, fluticasone propionate, budesonide, and the 22R-epimer of budesonide.

27. A pressurized metered dose inhaler according to claim 25, wherein said pharmaceutical formulation comprises at least one anticholinergic drug selected from the group consisting of ipratropium bromide, oxitropium bromide, and tiotropium bromide.

28. A pressurized metered dose inhaler according to claim 15, wherein said ethanol is present in said pharmaceutical formulation in an amount between 10 and 15% w/w.

29. A pressurized metered dose inhaler according to claim 15, wherein said active ingredient is (R,R)(−)formoterol fumarate.

30. A pressurized metered dose inhaler according to claim 15, wherein said 1M hydrochloric acid is present in said pharmaceutical formulation in a concentration between 0.035% w/w and 0.040% w/w.

31. A pressurized metered dose inhaler according to claim 15, wherein said pharmaceutical formulation comprises 0.006-0.048% w/v formoterol fumarate, 10-15% w/w anhydrous ethanol, hydrochloric acid in an amount equal to 0.030-0.045% w/w of 1M hydrochloric acid, and HFA 134a.

32. A method of preparing a container which contains a pharmaceutical formulation which comprises:
an active ingredient selected from the group consisting of formoterol, a stereoisomer of formoterol, and a physiologically acceptable salt of formoterol, in a solution of a liquefied HFA propellant;
ethanol as a co-solvent; and
hydrochloric acid,
wherein said ethanol is in anhydrous form and is present in a concentration between 10% and 20% w/w, and said hydrochloric acid is present in an amount equal to between 0.030% and 0.045% w/w of 1M hydrochloric acid, and any water present in said pharmaceutical formulation is present in an amount lower than 1500 ppm based on the total weight of said pharmaceutical formulation,
said method comprising:
(a) preparing a first solution comprising said active ingredient, in anhydrous ethanol;
(b) adding hydrochloric acid, to said first solution to obtain an second solution;
(c) filling a container with said second solution;
(d) crimping said container with a valve and gassing;
(e) adding a propellant which comprises a hydrofluoroalkane
wherein said container is a standard aluminum can.

* * * * *